United States Patent
Jensen (10) Patent No.: US 12,410,172 B2
(45) Date of Patent: Sep. 9, 2025

(54) CRYSTALLINE FORMS OF 3-CYANO-1-[4-[6-(1- METHYL-1H-PYRAZOL-4-YL) PYRAZOLO[1,5-A]PYRAZIN-4-YL]-1H-PYRAZOL-1-YL]CYCLOBUTANEACE-TONITRILE, AND USE THEREOF

(71) Applicant: PFIZER INC., New York, NY (US)

(72) Inventor: Andrew James Jensen, Groton, CT (US)

(73) Assignee: PFIZER INC., New York, NY (US)

( * ) Notice: Subject to any disclaimer, the term of this patent is extended or adjusted under 35 U.S.C. 154(b) by 380 days.

(21) Appl. No.: 17/917,160

(22) PCT Filed: Apr. 5, 2021

(86) PCT No.: PCT/IB2021/052812
§ 371 (c)(1),
(2) Date: Oct. 5, 2022

(87) PCT Pub. No.: WO2021/205322
PCT Pub. Date: Oct. 14, 2021

(65) Prior Publication Data
US 2023/0159539 A1 May 25, 2023

Related U.S. Application Data

(60) Provisional application No. 63/133,567, filed on Jan. 4, 2021, provisional application No. 63/007,095, filed on Apr. 8, 2020.

(51) Int. Cl.
C07D 487/04 (2006.01)
(52) U.S. Cl.
CPC ........ *C07D 487/04* (2013.01); *C07B 2200/13* (2013.01)
(58) Field of Classification Search
CPC .................... C07D 487/04; C07B 2200/13
See application file for complete search history.

(56) References Cited

U.S. PATENT DOCUMENTS

| | | | | |
|---|---|---|---|---|
| 2012/0258976 A1* | 10/2012 | Murphy | ................. | A61P 43/00 544/280 |
| 2017/0240552 A1* | 8/2017 | Brown | ................. | A61P 37/00 |
| 2019/0040043 A1* | 2/2019 | Fenster | ................. | A61P 17/00 |

FOREIGN PATENT DOCUMENTS

| | | |
|---|---|---|
| JP | 2019510003 A | 4/2019 |
| WO | 2017144995 A1 | 8/2017 |

OTHER PUBLICATIONS

Javadzadeh et al. "Recrystallization of Drugs—Effect on Dissolution Rate". Recrystallization in Materials Processing, InTech, Oct. 28, 2015. Crossref, doi:10.5772/60006, pp. 191-211. (Year: 2015).*
Written Opinion for corresponding International (PCT) Application PCT/IB/2021/052812, 5 pages, dated May 27, 2021.
International Search Report for corresponding International (PCT) Application PCT/IB/2021/052812, 3 pages, dated May 27, 2021.
Taiwan Office Action and Search Report for the corresponding Taiwanese patent application, 110112518, 13 pages dated Sep. 13, 2022.
Wrobleski et al. "Highly Selective Inhibition of Tyrosine Kinase 2 (TYK2) for the Treatment of Autoimmune Diseases: Discovery of the Allosteric Inhibitor BMS-986165", Journal of Medicinal Chemistry, Jul. 18, 2019.

* cited by examiner

*Primary Examiner* — Doan T Phan
(74) *Attorney, Agent, or Firm* — Lisa Mueller; Tristan A. Fuierer; Casimir Jones SC (57) ABSTRACT

The present invention discloses novel crystalline forms of (1R,3R)-3-(cyanomethyl)-3-(4-(6-(1-methyl-1H-pyrazol-4-yl)pyrazolo[1,5-a]pyrazin-4-yl)-1H-pyrazol-1-yl)cyclobutane-1-carbonitrile, Form 1 anhydrous free base and Form 2 monohydrate, pharmaceutical composition containing them, preparations thereof and uses thereof.

20 Claims, 6 Drawing Sheets

CRYSTALLINE FORMS OF 3-CYANO-1-[4-[6-(1-METHYL-1H-PYRAZOL-4-YL)PYRAZOLO[1,5-A]PYRAZIN-4-YL]-1H-PYRAZOL-1-YL]CYCLOBUTANEACETONITRILE, AND USE THEREOF

CROSS-REFERENCE TO RELATED APPLICATIONS

The present application is a national stage application of PCT Application No. PCT/IB2021/052812, filed Apr. 5, 2021, which claims priority based on U.S. Provisional Applications 63/133,567 and 63/007,095, filed Jan. 4, 2021 and Apr. 8, 2020, respectively, the contents of all of which are incorporated herein in their entireties.

FIELD OF THE DISCLOSURE

The present disclosure relates to a crystalline form of (1R,3R)-3-(cyanomethyl)-3-(4-(6-(1-methyl-1H-pyrazol-4-yl)pyrazolo[1,5-a]pyrazin-4-yl)-1H-pyrazol-1-yl)cyclobutane-1-carbonitrile, Form 1 anhydrous free base. The present disclosure also relates to a crystalline form of (1R,3R)-3-(cyanomethyl)-3-(4-(6-(1-methyl-1H-pyrazol-4-yl)pyrazolo[1,5-a]pyrazin-4-yl)-1H-pyrazol-1-yl)cyclobutane-1-carbonitrile, Form 2 monohydrate. The present disclosure also relates to pharmaceutical compositions comprising either said crystalline form, and to methods for preparing them. The disclosure further relates to the use of either said crystalline forms in the treatment of various diseases.

BACKGROUND OF THE DISCLOSURE (1R,3R)-3-(Cyanomethyl)-3-(4-(6-(1-methyl-1H-pyrazol-4-yl)pyrazolo[1,5-a]pyra-zin-4-yl)-1H-pyrazol-1-yl)cyclobutane-1-carbonitrile has the chemical formula $C_{20}H_{17}N_9$ and the following structural formula:

The synthesis of (1R,3R)-3-(cyanomethyl)-3-(4-(6-(1-methyl-1H-pyrazol-4-yl)pyrazolo[1,5-a]pyrazin-4-yl)-1H-pyrazol-1-yl)cyclobutane-1-carbonitrile is described in commonly assigned U.S. Pat. No. 10,144,738, the contents of which are incorporated herein by reference in its entirety. The crystalline forms of (1R,3R)-3-(cyanomethyl)-3-(4-(6-(1-methyl-1H-pyrazol-4-yl)pyrazolo[1,5-a]pyrazin-4-yl)-1H-pyrazol-1-yl)cyclobut-ane-1-carbonitrile, Form 1 free base anhydrous, and Form 2 monohydrate, are useful as inhibitors of protein kinases, such as the enzyme Janus Kinase (JAK) and as such are useful therapeutically as an immunosuppressive agent for organ transplants, xenotransplantation, lupus, multiple sclerosis, rheumatoid arthritis, psoriatic arthritis, inflammatory bowel disease (IBD), psoriasis, Type 1 diabetes and complications from diabetes, cancer, asthma, atopic dermatitis, autoimmune thyroid disorders, ulcerative colitis, Crohn's disease, Alzheimer's disease, Leukemia and other indications where immunosuppression would be desirable. The present disclosure relates to novel solid forms of the anhydrous free base and monohydrate of (1R,3R)-3-(cyanomethyl)-3-(4-(6-(1-methyl-1H-pyrazol-4-yl)pyrazolo[1,5-a]pyrazin-4-yl)-1H-pyrazol-1-yl)cyclobutane-1-carbonitrile that possess improved material properties for use in the manufacture of a pharmaceutical dosage form.

Based on a chemical structure, one cannot predict with any degree of certainty whether a compound will crystallize, under what conditions it will crystallize, how many crystalline solid forms of the compound might exist, or the solid-state structure of any of those forms. A key characteristic of any crystalline drug is the polymorphic behavior of such a material. In general, crystalline forms of drugs are preferred over noncrystalline forms of drugs and drug intermediates, in part, because of their superior stability. For example, in many situations, a noncrystalline drug is observed to convert to a crystalline drug form upon storage. Because noncrystalline and crystalline forms of a drug typically have differing physical properties and chemical properties, such interconversion may be undesirable for safety reasons in pharmaceutical usage. The different physical properties exhibited by different solid forms of a pharmaceutical compound can affect important pharmaceutical parameters such as storage, stability, compressibility, density (important in formulation and product manufacturing), and dissolution rates (important in determining bioavailability). Stability differences may result from changes in chemical reactivity (e.g., differential hydrolysis or oxidation, such that a dosage form comprising a certain polymorph can discolor more rapidly than a dosage form comprising a different polymorph), mechanical changes (e.g., tablets can crumble on storage as a kinetically favored crystalline form converts to thermodynamically more stable crystalline form), or both (e.g., tablets of one polymorph can be more susceptible to breakdown at high humidity).

Solubility differences between polymorphs may, in extreme situations, result in transitions to crystalline forms that lack potency or result in overexposure. In addition, the physical properties of a crystalline form may also be important in pharmaceutical processing. For example, a particular crystalline form may form solvates more readily or may be more difficult to filter and wash free of impurities than other crystalline forms (i.e., particle shape and size distribution might be different between one crystalline form relative to other forms).

There is no one ideal physical form of a drug because different physical forms provide different advantages. The search for the most stable form is arduous and the outcome is unpredictable. Thus, it is important to seek a variety of unique drug forms, e.g., salts, polymorphs, non-crystalline forms, which may be used in various formulations. The selection of a drug form for a specific formulation or therapeutic application requires consideration of a variety of properties, and the best form for a particular application may be one which has one specific important good property while other properties may be acceptable or marginally acceptable.

The successful development of a drug requires that it meet certain general requirements to be a therapeutically effective treatment for patients. These requirements fall into two categories: (1) requirements for successful manufacture of dosage forms, and (2) requirements for successful drug delivery and disposition after the drug formulation has been administered to the patient.

Different crystalline solid forms of the same compound often possess different solid-state properties such as melting point, solubility, dissolution rate, hygroscopicity, powder flow, mechanical properties, chemical stability and physical stability. These solid-state properties may offer advantages in filtration, drying, and dosage form manufacturing unit operations. Thus, once different crystalline solid forms of the same compound have been identified, the optimum crystalline solid form under any given set of processing and manufacturing conditions may be determined as well as the different solid-state properties of each crystalline solid form.

Polymorphs of a molecule can be obtained by a number of methods known in the art. Such methods include, but are not limited to, melt recrystallization, melt cooling, solvent recrystallization, desolvation, rapid evaporation, rapid cooling, slow cooling, vapor diffusion and sublimation. Polymorphs can be detected, identified, classified and characterized using well-known techniques such as, but not limited to, differential scanning calorimetry (DSC), thermogravimetry (TGA), X-ray powder diffractometry (XRPD), single crystal X-ray diffractometry, solid state nuclear magnetic resonance (NMR), infrared (IR) spectroscopy, Raman spectroscopy, and hot-stage optical microscopy.

The present disclosure is directed to a crystalline form of (1R,3R)-3-(cyanomethyl)-3-(4-(6-(1-methyl-1H-pyrazol-4-yl)pyrazolo[1,5-a]pyrazin-4-yl)-1H-pyrazol-1-yl)cyclobutane-1-carbonitrile, Form 1 anhydrous free base. The present disclosure also relates to a crystalline form of (1R,3R)-3-(cyanomethyl)-3-(4-(6-(1-methyl-1H-pyrazol-4-yl)pyrazolo[1,5-a]pyrazin-4-yl)-1H-pyrazol-1-yl)cyclobutane-1-carbonitrile, Form 2 monohydrate. The disclosure is also directed to compositions, including pharmaceutical compositions, containing crystalline (1R,3R)-3-(cyanomethyl)-3-(4-(6-(1-methyl-1H-pyrazol-4-yl)pyrazolo[1,5-a]pyrazin-4-yl)-1H-pyrazol-1-yl)cyclobutane-1-carbonitrile, either Form 1 anhydrous free base, or Form 2 monohydrate. The disclosure is further directed to processes for preparing crystalline (1R,3R)-3-(cyanomethyl)-3-(4-(6-(1-methyl-1H-pyrazol-4-yl)pyrazolo[1,5-a]pyrazin-4-yl)-1H-pyrazol-1-yl)cyclobutane-1-carbonitrile, Form 1 anhydrous free base, and Form 2 monohydrate.

Because drug formulations, showing, for example, enhanced bioavailability or stability are consistently sought, there is an ongoing need for new or purer polymorphic forms of drug molecules. The crystalline forms of (1R,3R)-3-(cyanomethyl)-3-(4-(6-(1-methyl-1H-pyrazol-4-yl)pyrazolo[1,5-a]pyrazin-4-yl)-1H-pyrazol-1-yl)cyclobutane-1-carbonitrile, Form 1 anhydrous free base, and Form 2 monohydrate, described herein help meet these and other needs.

SUMMARY OF THE DISCLOSURE

The present disclosure provides a crystalline form of (1R,3R)-3-(cyanomethyl)-3-(4-(6-(1-methyl-1H-pyrazol-4-yl)pyrazolo[1,5-a]pyrazin-4-yl)-1H-pyrazol-1-yl)cyclobutane-1-carbonitrile Form 1 anhydrous free base.

Figure 1:
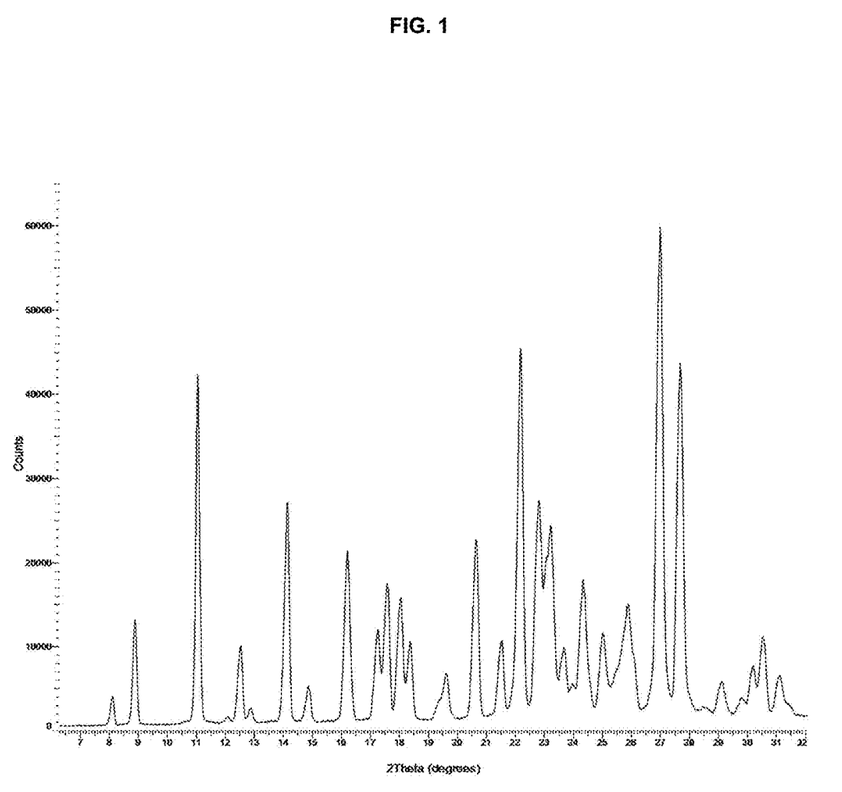
FIG. 1 depicts a powder X-ray diffraction pattern of the crystalline form of (1R,3R)-3-(cyanomethyl)-3-(4-(6-(1-methyl-1H-pyrazol-4-yl)pyrazolo[1,5-a]pyrazin-4-yl)-1H-pyrazol-1-yl)cyclobutane-1-carbonitrile Form 1 anhydrous free base.
Figure 3:
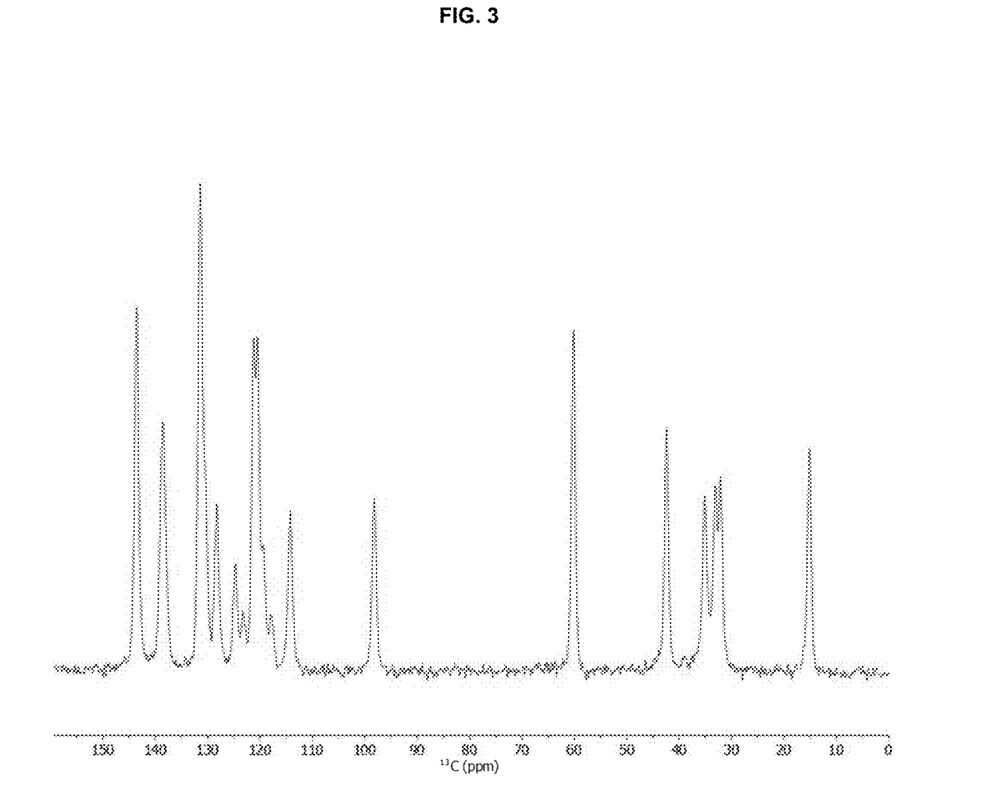
FIG. 3 depicts a solid state $^{13}$C nuclear magnetic resonance spectrum of the crystalline form of (1R,3R)-3-(cyanomethyl)-3-(4-(6-(1-methyl-1H-pyrazol-4-yl)pyrazolo[1,5-a]pyrazin-4-yl)-1H-pyrazol-1-yl)cyclobutane-1-carbonitrile Form 1 anhydrous free base.
Figure 4:
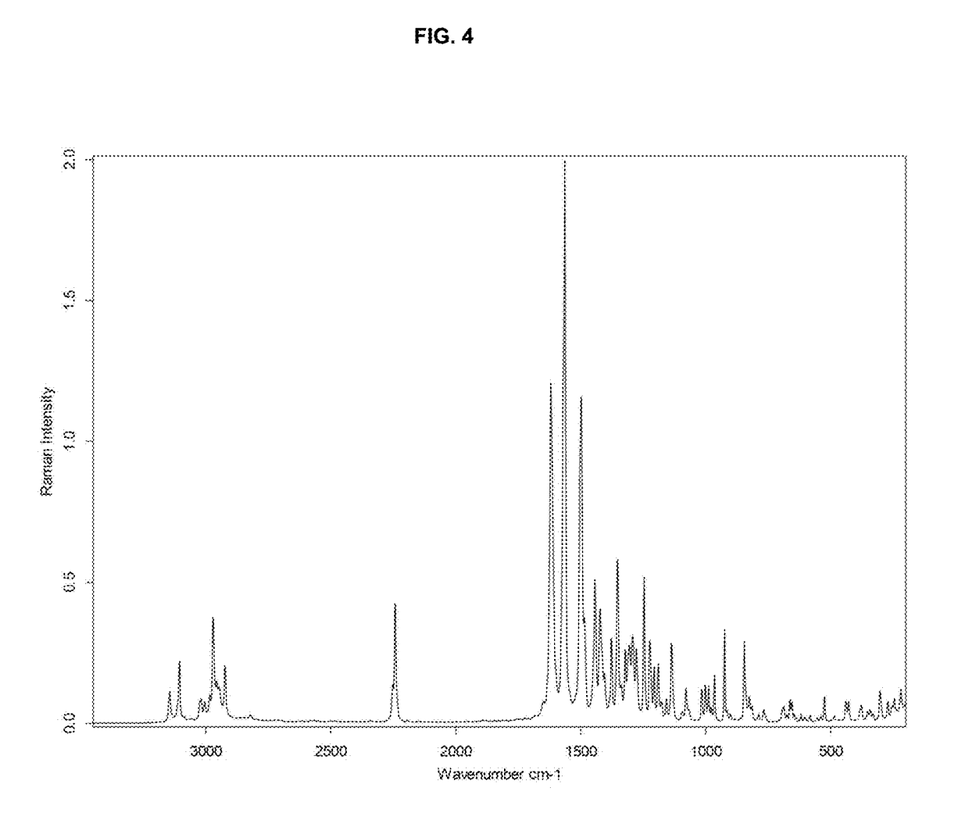
FIG. 4 depicts a Raman spectrum of the crystalline form of (1R,3R)-3-(cyanomethyl)-3-(4-(6-(1-methyl-1H-pyrazol-4-yl)pyrazolo[1,5-a]pyrazin-4-yl)-1H-pyrazol-1-yl)cyclobutane-1-carbonitrile Form 1 anhydrous free base.

In one aspect, the present disclosure comprises a crystalline form of (1R,3R)-3-(cyanomethyl)-3-(4-(6-(1-methyl-1H-pyrazol-4-yl)pyrazolo[1,5-a]pyrazin-4-yl)-1H-pyrazol-1-yl)cyclobutane-1-carbonitrile Form 1 anhydrous free base, having one or more characteristics selected from the group consisting of:

I) a powder X-ray powder diffraction pattern comprising: (a) one, two, three, four, five, or more than five peaks selected from the group consisting of the peaks in Table 1 in ° 2θ±0.2°2θ; or, (b) peaks at 2θ values essentially the same as shown in FIG. 1;

II) a Raman spectrum comprising: (a) one, two, three, four, five, or more than five wavenumber ($cm^{-1}$) values selected from the group consisting of the values in Table 5 in $cm^{-1}$±2 $cm^{-1}$; (b) one, two, three, four, five, or more than five wavenumber ($cm^{-1}$) values selected from the group consisting of the characteristic values in Table 5 in $cm^{-1}$±2 $cm^{-1}$; or (c) wavenumber ($cm^{-1}$) values essentially the same as shown in FIG. 4;

III) a $^{13}C$ solid state NMR spectrum (ppm) comprising: (a) one, two, three, four, five, or more than five resonance (ppm) values selected from the group consisting of the values in Table 3 in ppm±0.2 ppm; (b) one, two, three, four, five, or more than five resonance (ppm) values selected from the group consisting of the characteristic values in Table 3 in ppm±0.2 ppm; or (c) resonance (ppm) values essentially the same as shown in FIG. 3; and, IV) a combination of any two or three of the foregoing embodiments (I)(a)-(b), (II)(a)-(c), or (III)(a)-(c), provided they are not inconsistent with each other.

The present disclosure provides a crystalline form of (1R,3R)-3-(cyanomethyl)-3-(4-(6-(1-methyl-1H-pyrazol-4-yl)pyrazolo[1,5-a]pyrazin-4-yl)-1H-pyrazol-1-yl)cyclobutane-1-carbonitrile Form 2 monohydrate.

Figure 2:
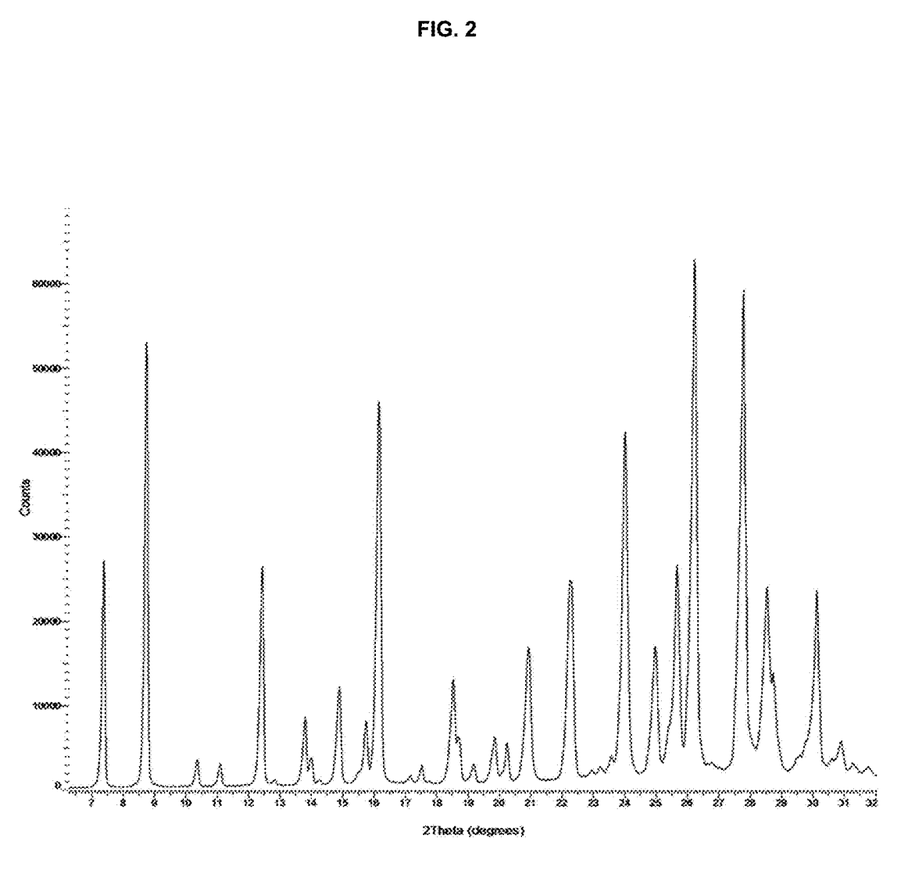
FIG. 2 depicts a powder X-ray diffraction pattern of the crystalline form of (1R,3R)-3-(cyanomethyl)-3-(4-(6-(1-methyl-1H-pyrazol-4-yl)pyrazolo[1,5-a]pyrazin-4-yl)-1H-pyrazol-1-yl)cyclobutane-1-carbonitrile Form 2 monohydrate.
Figure 5:
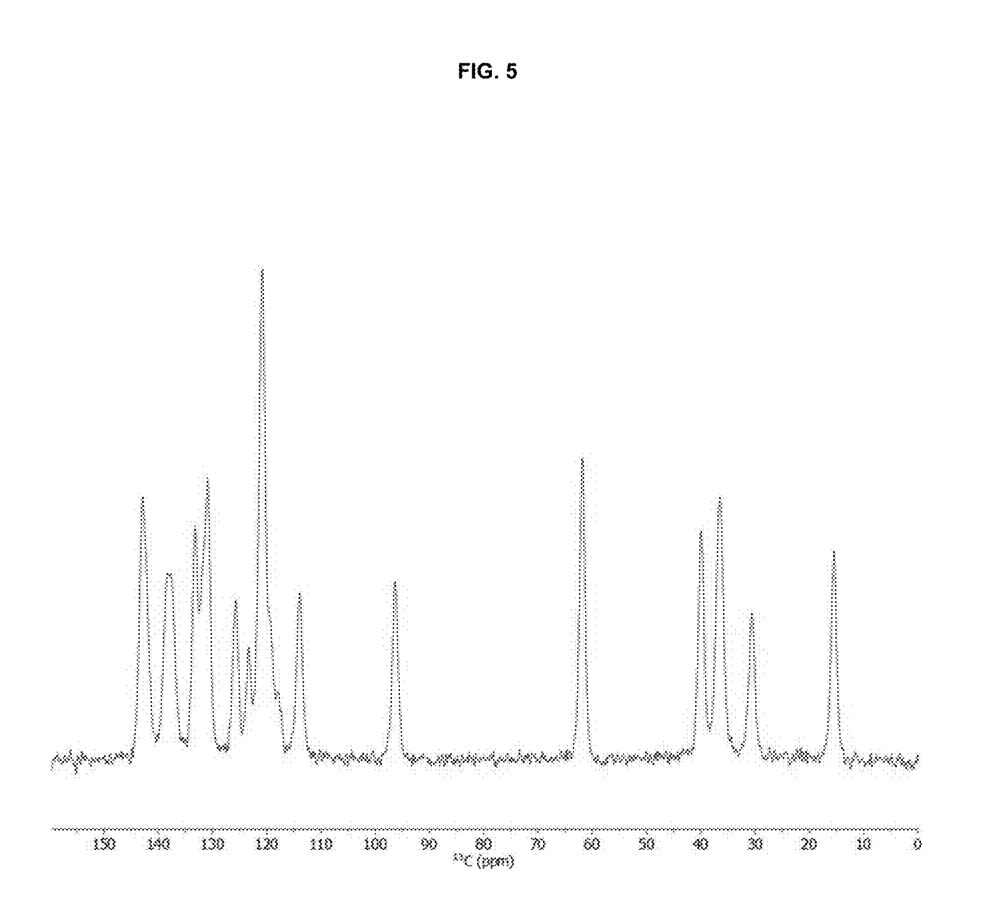
FIG. 5 depicts a solid state $^{13}$C nuclear magnetic resonance spectrum of the crystalline form of (1R,3R)-3-(cyanomethyl)-3-(4-(6-(1-methyl-1H-pyrazol-4-yl)pyrazolo[1,5-a]pyrazin-4-yl)-1H-pyrazol-1-yl)cyclobutane-1-carbonitrile Form 2 monohydrate.
Figure 6:
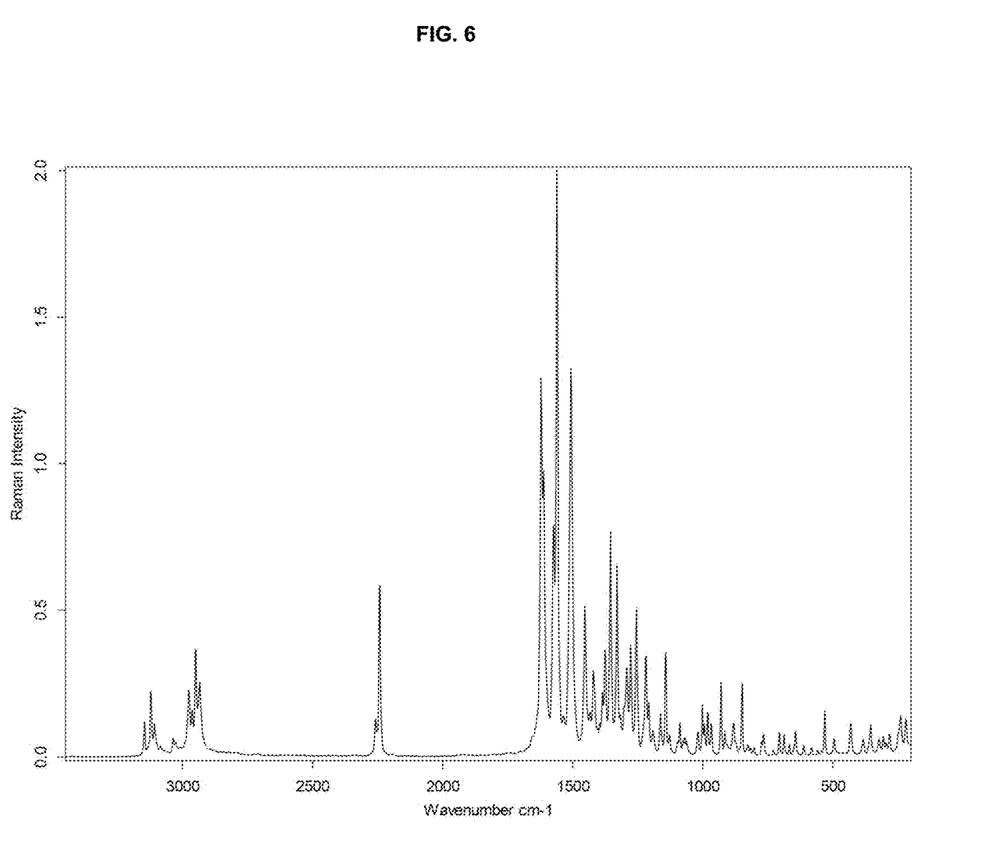
FIG. 6 depicts a Raman spectrum of the crystalline form of (1R,3R)-3-(cyanomethyl)-3-(4-(6-(1-methyl-1H-pyrazol-4-yl)pyrazolo[1,5-a]pyrazin-4-yl)-1H-pyrazol-1-yl)cyclobutane-1-carbonitrile Form 2 monohydrate.

In another aspect, the present disclosure comprises a crystalline form of (1R,3R)-3-(cyanomethyl)-3-(4-(6-(1-methyl-1H-pyrazol-4-yl)pyrazolo[1,5-a]pyrazin-4-yl)-1H-pyrazol-1-yl)cyclobutane-1-carbonitrile Form 2 monohydrate, having one or more characteristics selected from the group consisting of:

I) a powder X-ray powder diffraction pattern comprising: (a) one, two, three, four, five, or more than five peaks selected from the group consisting of the peaks in Table 2 in ° 2θ±0.2 °2θ; or, (b) peaks at 2θ values essentially the same as shown in FIG. 2;

II) a Raman spectrum comprising: (a) one, two, three, four, five, or more than five wavenumber ($cm^{-1}$) values selected from the group consisting of the values in Table 6 in $cm^{-1}$±2 $cm^{-1}$; (b) one, two, three, four, five, or more than five wavenumber ($cm^{-1}$) values selected from the group consisting of the characteristic values in Table 6 in $cm^{-1}$±2 $cm^{-1}$; or (c) wavenumber ($cm^{-1}$) values essentially the same as shown in FIG. 6;

III) a $^{13}C$ solid state NMR spectrum (ppm) comprising: (a) one, two, three, four, five, or more than five resonance (ppm) values selected from the group consisting of the values in Table 4 in ppm±0.2 ppm; (b) one, two, three, four, five, or more than five resonance (ppm) values selected from the group consisting of the characteristic values in Table 4 in ppm±0.2 ppm; or (c) resonance (ppm) values essentially the same as shown in FIG. 5; and, IV) a combination of any two or three of the foregoing embodiments (1)(a)-(b), (II)(a)-(c), or (III)(a)-(c), provided they are not inconsistent with each other.

In another aspect, the present disclosure also provides a pharmaceutical composition comprising crystalline (1R,3R)-3-(cyanomethyl)-3-(4-(6-(1-methyl-1H-pyrazol-4-yl)pyrazolo[1,5-a]pyrazin-4-yl)-1H-pyrazol-1-yl)cyclobutane-1-carbonitrile Form 1, anhydrous free base and a pharmaceutically acceptable carrier.

In another aspect, the present disclosure also provides a method of treating a disease in a mammal, comprising administering to a mammal in need thereof a therapeutically effective amount of crystalline (1R,3R)-3-(cyanomethyl)-3-(4-(6-(1-methyl-1H-pyrazol-4-yl)pyrazolo[1,5-a]pyrazin-4-yl)-1H-pyrazol-1-yl)cyclobutane-1-carbonitrile Form 1, anhydrous free base, or a pharmaceutically acceptable salt thereof or a pharmaceutical composition according to any of the embodiments described herein, said disease being selected from rheumatoid arthritis, lupus, psoriasis, psoriatic arthritis, atopic dermatitis, and inflammatory bowel disease.

In another aspect, the present disclosure also provides a pharmaceutical composition comprising crystalline (1R,3R)-3-(cyanomethyl)-3-(4-(6-(1-methyl-1H-pyrazol-4-yl)pyrazolo[1,5-a]pyrazin-4-yl)-1H-pyrazol-1-yl)cyclobutane-1-carbonitrile Form 2 monohydrate and a pharmaceutically acceptable carrier.

In another aspect, the present disclosure also provides a method of treating a disease in a mammal, comprising administering to a mammal in need thereof a therapeutically effective amount of crystalline (1R,3R)-3-(cyanomethyl)-3-(4-(6-(1-methyl-1H-pyrazol-4-yl)pyrazolo[1,5-a]pyrazin-4-yl)-1H-pyrazol-1-yl)cyclobutane-1-carbonitrile Form 2 monohydrate, or a pharmaceutically acceptable salt thereof or a pharmaceutical composition according to any of the embodiments described herein, said disease being selected from rheumatoid arthritis, lupus, psoriasis, psoriatic arthritis, atopic dermatitis, and inflammatory bowel disease.

DETAILED DESCRIPTION OF THE DISCLOSURE

The present disclosure is directed to crystalline forms of (1R,3R)-3-(cyanomethyl)-3-(4-(6-(1-methyl-1H-pyrazol-4-yl)pyrazolo[1,5-a]pyrazin-4-yl)-1H-pyrazol-1-yl)cyclobutane-1-carbonitrile including Form 1 anhydrous free base and Form 2 monohydrate. The present disclosure is also directed to pharmaceutical compositions comprising each crystalline form, and to methods for preparing such forms. The disclosure is further directed to the use of the crystalline forms in the treatment of various diseases.

There are a number of analytical methods one of ordinary skill in the art in solid-state chemistry can use to analyze solid forms. The term "analyze" as used herein means to obtain information about the solid-state structure of solid forms. For example, powder X-ray diffraction is a suitable technique for differentiating amorphous solid forms from crystalline solid forms and for characterizing and identifying crystalline solid forms of a compound. Powder X-ray diffraction (PXRD) is also suitable for quantifying the amount of a crystalline solid form (or forms) in a mixture. In powder X-ray diffraction, X-rays are directed onto a crystalline powder and the intensity of the diffracted X-rays is measured as a function of the angle between the X-ray source and the beam diffracted by the sample. The intensity of these diffracted X-rays can be plotted on a graph as peaks with the x-axis being the angle (this is known as the "2θ" angle) between the X-ray source and the diffracted X-rays and with the y-axis being the intensity of the diffracted X-rays. This graph is called a powder X-ray diffraction pattern or powder pattern. Different crystalline solid forms exhibit different powder patterns because the location of the peaks on the x-axis is a property of the solid-state structure of the crystal.

Such powder patterns, or portions thereof, can be used as an identifying fingerprint for a crystalline solid form. Thus, one could take a powder pattern of an unknown sample and compare that powder pattern with a reference powder pattern. A positive match would mean that the unknown sample is of the same crystalline solid form as that of the reference. One could also analyze an unknown sample containing a mixture of solid forms by adding and subtracting powder patterns of known compounds.

When selecting peaks in a powder pattern to characterize a crystalline solid form or when using a reference powder pattern to identify a form, one identifies a peak or collection of peaks in one form that are not present in the other solid forms.

The term "characterize" as used herein means to select an appropriate set of data capable of distinguishing one solid form from another. That set of data in powder X-ray diffraction is the position of one or more peaks. Selecting which powder X-ray diffraction peaks define a particular form is said to characterize that form.

The term "identify" as used herein means taking a selection of characteristic data for a solid form and using those data to determine whether that form is present in a sample. In powder X-ray diffraction, those data are the x-axis positions of the one or more peaks characterizing the form in question as discussed above. For example, once one determines that a select number of X-ray diffraction peaks characterize a particular solid form, one can use those peaks to determine whether that form is present in a sample.

When characterizing and/or identifying crystalline solid forms of the same chemical compound with powder X-ray diffraction, it is often not necessary to use the entire powder pattern. A smaller subset of the entire powder pattern can often be used to perform the characterization and/or identification. By selecting a collection of peaks that differentiate the crystalline solid form from other crystalline solid forms of the compound, one can rely on those peaks to both characterize the form and to identify the form in, for example, an unknown mixture. Additional data can be added, such as from another analytical technique or additional peaks from the powder pattern, to characterize and/or identify the form should, for instance, additional polymorphs be identified later.

Due to differences in instruments, samples, and sample preparation, peak values are sometimes reported with the modifier "about" in front of the peak values. This is common practice in the solid-state chemical arts because of the variation inherent in peak values. A typical precision of the 2θ x-axis value of a peak in a powder pattern is on the order of plus or minus 0.2° 2θ. Thus, a diffraction peak that appears at "about 9.2° 2θ," means that the peak could be between 9.0° 2θ and 9.4° 2θ when measured on most X-ray diffractometers under most conditions. Variability in peak intensity is a result of how individual crystals are oriented in the sample container with respect to the external X-ray source (known as "preferred orientation"). This orientation effect does not provide structural information about the crystal.

Powder X-ray diffraction is just one of several analytical techniques one may use to characterize and/or identify crystalline solid forms. Spectroscopic techniques such as Raman (including microscopic Raman), infrared, and solid state NMR spectroscopies may be used to characterize and/or identify crystalline solid forms. These techniques may also be used to quantify the amount of one or more crystalline solid forms in a mixture and peak values can also be reported with the modifier "about" in front of the peak values. A typical variability for a peak value associated with an FT-Raman and FT-Infrared measurement is on the order of plus or minus 2 cm$^{-1}$. A typical variability for a peak value associated with a $^{13}$C or 19F chemical shift is on the order of plus or minus 0.2 ppm for crystalline material. A typical variability for a value associated with a differential scanning calorimetry onset temperature is on the order of plus or minus 5° C.

The term "room temperature" as used herein refers to the temperature range of 20° C. to 23° C. In the first aspect, the present disclosure comprises a crystalline form of (1R,3R)-3-(cyanomethyl)-3-(4-(6-(1-methyl-1H-pyrazol-4-yl)pyrazolo[1,5-a]pyrazin-4-yl)-1H-pyrazol-1-yl)cyclobutane-1-carbonitrile Form 1 anhydrous free base having one or more characteristics selected from the group consisting of:
  I) a powder X-ray diffraction pattern containing the following 2θ values measured using Cu wavelength radiation: 20.6°, 22.8° and 27.0° 2θ±0.2° 2θ;
  II) a powder X-ray diffraction pattern containing the following 2θ values measured using Cu wavelength radiation: 18.0°, 20.6°, 22.8° and 27.0° 2θ±0.2° 2θ; and,
  III) a powder X-ray diffraction pattern containing the following 2θ values measured using Cu wavelength radiation: 8.1°, 18.0°, 20.6°, 22.8° and 27.0° 2θ±0.2° 2θ.

Accordingly, the disclosure provides a crystalline form of (1R,3R)-3-(cyanomethyl)-3-(4-(6-(1-methyl-1H-pyrazol-4-yl)pyrazolo[1,5-a]pyrazin-4-yl)-1H-pyrazol-1-yl)cyclobutane-1-carbonitrile, having a powder X-ray diffraction pattern comprising peaks, in terms of 2θ, at 20.6°, 22.8° and 27.0° 2θ±0.2° 2θ. The disclosure also provides a crystalline form of (1R,3R)-3-(cyanomethyl)-3-(4-(6-(1-methyl-1H-pyrazol-4-yl)pyrazolo[1,5-a]pyrazin-4-yl)-1H-pyrazol-1-yl)cyclobutane-1-carbonitrile, having a powder X-ray diffraction pattern comprising peaks, at 18.0°, 20.6°, 22.8° and 27.0° 2θ±0.2° 2θ. The disclosure further provides a crystalline form of (1R,3R)-3-(cyanomethyl)-3-(4-(6-(1-methyl-1H-pyrazol-4-yl)pyrazolo[1,5-a]pyrazin-4-yl)-1H-pyrazol-1-yl)cyclobutane-1-carbonitrile, having a powder X-ray diffraction pattern comprising peaks at 8.1°, 18.0°, 20.6°, 22.8° and 27.0° 2θ±0.2° 2θ.

In addition, the disclosure provides a pharmaceutical composition comprising a crystalline form of (1R,3R)-3-(cyanomethyl)-3-(4-(6-(1-methyl-1H-pyrazol-4-yl)pyrazolo[1,5-a]pyrazin-4-yl)-1H-pyrazol-1-yl)cyclobutane-1-carbonitrile Form 1 anhydrous free base; and, a pharmaceutically acceptable carrier. In certain embodiments, the disclosure provides said pharmaceutical composition, wherein said crystalline form has a powder X-ray diffraction pattern comprising peaks at 20.6°, 22.8° and 27.0° 2θ±0.2° 2θ. In other embodiments, the disclosure provides said pharmaceutical composition, wherein said crystalline form has a powder X-ray diffraction pattern comprising peaks at 18.0°, 20.6°, 22.8° and 27.0° 2±0.2° 2θ. In yet other embodiments, the disclosure provides said pharmaceutical composition, wherein said crystalline form has a powder X-ray diffraction pattern comprising peaks at 8.1°, 18.0°, 20.6°, 22.8° and 27.0° 2θ±0.2° 2θ.

In the second aspect, the present disclosure comprises a crystalline form of (1R,3R)-3-(cyanomethyl)-3-(4-(6-(1-methyl-1H-pyrazol-4-yl)pyrazolo[1,5-a]pyrazin-4-yl)-1H-pyrazol-1-yl)cyclobutane-1-carbonitrile monohydrate (Form 2) having one or more characteristics selected from the group consisting of:
  I) a powder X-ray diffraction pattern containing the following 2θ values measured using Cu wavelength radiation: 7.4°, 26.2°, 28.5° 2θ±0.2° 2θ;
  II) a powder X-ray diffraction pattern containing the following 2θ values measured using Cu wavelength radiation: 7.4°, 15.7°, 26.2°, 28.5° 2θ±0.2° 2θ; and,
  III) a powder X-ray diffraction pattern containing the following 2θ values measured using Cu wavelength radiation: 7.4°, 10.4°, 15.7°, 26.2°, 28.5° 2θ±0.2° 2θ.

Accordingly, the disclosure provides a crystalline form of (1R,3R)-3-(cyanomethy)-3-(4-(6-(1-methyl-1H-pyrazol-4-yl)pyrazolo[1,5-a]pyrazin-4-yl)-1H-pyrazol-1-yl)cyclobutane-1-carbonitrile monohydrate, having a powder X-ray diffraction pattern comprising peaks, in terms of 2θ, at 7.4°, 26.2°, 28.5° 2θ±0.2° 2θ. The disclosure also provides a crystalline form of (1R,3R)-3-(cyanomethyl)-3-(4-(6-(1-methyl-1H-pyrazol-4-yl)pyrazolo[1,5-a]pyrazin-4-yl)-1H-pyrazol-1-yl)cyclobutane-1-carbonitrile monohydrate, having a powder X-ray diffraction pattern comprising peaks, at 7.4°, 15.7°, 26.2°, 28.5° 2θ±0.2° 2θ. The disclosure further provides a crystalline form of (1R,3R)-3-(cyanomethyl)-3-(4-(6-(1-methyl-1H-pyrazol-4-yl)pyrazolo[1,5-a]pyrazin-4-yl)-1H-pyrazol-1-yl)cyclobutane-1-carbonitrile monohydrate, having a powder X-ray diffraction pattern comprising peaks at 7.4°, 10.4°, 15.7°, 26.2°, 28.5° 2θ±0.2° 2θ.

In addition, the disclosure provides a pharmaceutical composition comprising a crystalline form of (1R,3R)-3-(cyanomethyl)-3-(4-(6-(1-methyl-1H-pyrazol-4-yl)pyrazolo[1,5-a]pyrazin-4-yl)-1H-pyrazol-1-yl)cyclobutane-1-carbonitrile monohydrate; and, a pharmaceutically acceptable carrier. In certain embodiments, the disclosure provides said pharmaceutical composition, wherein said crystalline form has a powder X-ray diffraction pattern comprising peaks at 7.4°, 26.2°, 28.5° 2θ±0.2° 2θ. In other embodiments, the disclosure provides said pharmaceutical composition, wherein said crystalline form has a powder X-ray diffraction pattern comprising peaks at 7.4°, 15.7°, 26.2°, 28.5° 2θ±0.2° 2θ. In yet other embodiments, the disclosure provides said pharmaceutical composition, wherein said crystalline form has a powder X-ray diffraction pattern comprising peaks at 7.4°, 10.4°, 15.7°, 26.2°, 28.5° 2θ±0.2° 2θ.

The disclosure also provides a pharmaceutical composition of said crystalline form, according to any of the embodiments described herein, comprising a topical formulation selected from a cream, transdermal patch, ointment, ophthalmic drops, lotion and gel. In certain embodiments, the disclosure provides said pharmaceutical composition wherein the topical formulation contains from about 0.1% to about 5.0% (w/v) crystalline (1R,3R)-3-(cyanomethyl)-3-(4-(6-(1-methyl-1H-pyrazol-4-yl)pyrazolo[1,5-a]pyrazin-4-yl)-1H-pyrazol-1-yl)cyclobutane-1-carbonitrile, Form 1 anhydrous free base or Form 2 monohydrate.

In addition, the disclosure provides a method of treating a disease in a mammal, comprising administering to a mammal in need thereof a therapeutically effective amount of a crystalline form of (1R,3R)-3-(cyanomethyl)-3-(4-(6-(1-methyl-1H-pyrazol-4-yl)pyrazolo[1,5-a]pyrazin-4-yl)-1H-pyrazol-1-yl)cyclobutane-1-carbonitrile, Form 1 anhydrous free base, or a pharmaceutically acceptable salt thereof, and a pharmaceutically acceptable carrier, wherein the disease is selected from the group consisting of lupus, rheumatoid arthritis, IBD, ulcerative colitis, Crohn's Disease, vitiligo, alopecia, psoriasis and atopic dermatitis. In certain embodiments, the disclosure provides said method, wherein said crystalline form has a powder X-ray diffraction pattern comprising peaks at 20.6°, 22.8° and 27.0° 2θ±0.2° 2θ. In certain other embodiments, the disclosure provides said crystalline form has a powder X-ray diffraction pattern comprising peaks at 18.0°, 20.6°, 22.8° and 27.0° 2θ±0.2° 2θ. In yet other certain embodiments, the disclosure provides said crystalline form has a powder X-ray diffraction pattern comprising peaks, in terms of 8.1°, 18.0°, 20.6°, 22.8° and 27.0° 2θ±0.2° 2θ.

The disclosure also provides a method of treating a disease in a mammal, comprising administering to a mammal in need thereof a therapeutically effective amount of a crystalline form of (1R,3R)-3-(cyanomethyl)-3-(4-(6-(1-methyl-1H-pyrazol-4-yl)pyrazolo[1,5-a]pyrazin-4-yl)-1H-pyrazol-1-yl)cyclobutane-1-carbonitrile, Form 2 monohydrate, or a pharmaceutically acceptable salt thereof, and a pharmaceutically acceptable carrier, wherein the disease is selected from the group consisting of lupus, rheumatoid arthritis, IBD, ulcerative colitis, Crohn's Disease, vitiligo, alopecia, psoriasis and atopic dermatitis. In certain embodiments, the disclosure provides said method, wherein said crystalline form has a powder X-ray diffraction pattern comprising peaks at 7.4°, 26.2°, 28.5° 2θ±0.2° 2θ. In certain other embodiments, the disclosure provides said crystalline form has a powder X-ray diffraction pattern comprising peaks at 7.4°, 15.7°, 26.2°, 28.5° 2θ±0.2° 2θ. In yet other certain embodiments, the disclosure provides said crystalline form has a powder X-ray diffraction pattern comprising peaks, in terms of 7.4°, 10.4°, 15.7°, 26.2°, 28.5° 2θ±0.2° 2θ.

The disclosure also provides a method of topically treating a disease in a mammal, comprising administering by a topical mode of administration to a mammal in need thereof a therapeutically effective amount of a crystalline form of (1R,3R)-3-(cyanomethyl)-3-(4-(6-(1-methyl-1H-pyrazol-4-yl)pyrazolo[1,5-a]pyrazin-4-yl)-1H-pyrazol-1-yl)cyclobutane-1-carbonitrile, Form 1 anhydrous free base, or a pharmaceutically acceptable salt thereof, and a pharmaceutically acceptable carrier, wherein the disease is selected from the group consisting of vitiligo, alopecia, psoriasis and atopic dermatitis In certain embodiments, the disclosure provides said method, wherein said crystalline form has a powder X-ray diffraction pattern comprising peaks at 20.6°, 22.8° and 27.0° 2θ±0.2° 2θ. In certain other embodiments, the disclosure provides said method where the crystalline form has a powder X-ray diffraction pattern comprising peaks at 18.0°, 20.6°, 22.8° and 27.0° 2θ±0.2° 2θ. In yet other certain embodiments, the disclosure provides said method where the crystalline form has a powder X-ray diffraction pattern comprising peaks, in terms of 8.1°, 18.0°, 20.6°, 22.8° and 27.0° 2θ±0.2° 2θ.

The disclosure also provides a method of topically treating a disease in a mammal, comprising administering by a topical mode of administration to a mammal in need thereof a therapeutically effective amount of a crystalline form of (1R,3R)-3-(cyanomethyl)-3-(4-(6-(1-methyl-1H-pyrazol-4-yl)pyrazolo[1,5-a]pyrazin-4-yl)-1H-pyrazol-1-yl)cyclobutane-1-carbonitrile, Form 2 monohydrate, or a pharmaceutically acceptable salt thereof, and a pharmaceutically acceptable carrier, wherein the disease is selected from the group consisting of vitiligo, alopecia, psoriasis and atopic dermatitis In certain embodiments, the disclosure provides said method, wherein said crystalline form has a powder X-ray diffraction pattern comprising peaks at 7.4°, 26.2°, 28.5° 2θ±0.2° 2θ. In certain other embodiments, the disclosure provides said method where the crystalline form has a powder X-ray diffraction pattern comprising peaks at 7.4°, 15.7°, 26.2°, 28.5° 2θ±0.2° 2θ. In yet other certain embodiments, the disclosure provides said method where the crystalline form has a powder X-ray diffraction pattern comprising peaks, in terms of 7.4°, 10.4°, 15.7°, 26.2°, 28.5° 2θ±0.2° 2θ.

Accordingly, the present disclosure provides pharmaceutical compositions comprising a crystalline form disclosed herein, and to methods for preparing such forms, as well as pharmaceutical compositions for use in medicine and for use in treating such diseases as lupus, rheumatoid arthritis, IBD, ulcerative colitis, Crohn's Disease, vitiligo, alopecia, psoriasis, psoriatic arthritis, and atopic dermatitis. The present disclosure also provides the use of such pharmaceutical compositions in the manufacture of a medicament for treating such diseases as lupus, rheumatoid arthritis, IBD, ulcerative colitis, Crohn's Disease, vitiligo, alopecia, psoriasis and atopic dermatitis.

The present disclosure further provides a crystalline form of (1R,3R)-3-(cyanomethyl)-3-(4-(6-(1-methyl-1H-pyrazol-4-yl)pyrazolo[1,5-a]pyrazin-4-yl)-1H-pyrazol-1-yl)cyclobutane-1-carbonitrile, prepared by re-crystallizing (1R,3R)-3-(cyanomethyl)-3-(4-(6-(1-methyl-1H-pyrazol-4-yl)pyrazolo[1,5-a]pyrazin-4-yl)-1H-pyrazol-1-yl)cyclobutane-1-carbonitrile, Form 1 anhydrous free base, from a suitable solvent. The present disclosure further provides a crystalline form of (1R,3R)-3-(cyanomethyl)-3-(4-(6-(1-methyl-1H-pyrazol-4-yl)pyrazolo[1,5-a]pyrazin-4-yl)-1H-pyrazol-1-yl)cyclobutane-1-carbonitrile, prepared by re-crystallizing (1R,3R)-3-(cyanomethyl)-3-(4-(6-(1-methyl-1H-pyrazol-4-yl)pyrazolo[1,5-a]pyrazin-4-yl)-1H-pyrazol-1-yl)cyclobut-ane-1-carbonitrile, Form 2 monohydrate, from a suitable solvent.

The present disclosure also provides a topical formulation of (1R,3R)-3-(cyanomethyl)-3-(4-(6-(1-methyl-1H-pyrazol-4-yl)pyrazolo[1,5-a]pyrazin-4-yl)-1H-pyrazol-1-yl)cyclobutane-1-carbonitrile, Form 1 anhydrous free base, or Form 2 monohydrate, prepared by combining a crystalline form thereof with excipients suitable for transdermal administration.

Methods of treating the diseases and syndromes listed herein are understood to involve administering to an individual in need of such treatment a therapeutically effective amount of the polymorph of the disclosure, or a composition containing the same. As used herein, the term "treating" in reference to a disease is meant to refer to preventing, inhibiting and/or ameliorating the disease.

As used herein, the term "individual" or "patient," used interchangeably, refers to any animal, including mammals, preferably mice, rats, other rodents, rabbits, dogs, cats, swine, cattle, sheep, goats, horses, or primates, and most preferably humans. As used herein, the phrase "therapeutically effective amount" refers to the amount of active compound or pharmaceutical agent that elicits the biological or medicinal response in a tissue, system, animal, individual or human that is being sought by a researcher, veterinarian, medical doctor or other clinician, which includes one or more of the following:

(1) preventing the disease; for example, preventing a disease, condition or disorder in an individual that may be predisposed to the disease, condition or disorder but does not yet experience or display the pathology or symptomatology of the disease;

(2) inhibiting the disease; for example, inhibiting a disease, condition or disorder in an individual that is experiencing or displaying the pathology or symptomatology of the disease, condition or disorder (i.e., arresting or slowing further development of the pathology and/or symptomatology); and (3) ameliorating the disease; for example, ameliorating a disease, condition or disorder in an individual that is experiencing or displaying the pathology or symptomatology of the disease, condition or disorder (i.e., reversing the pathology and/or symptomatology).

Dosage and Formulation

The disclosure also includes pharmaceutical compositions utilizing one or more of the present crystalline forms along with one or more pharmaceutically acceptable carriers, excipients, vehicles, etc.

The crystalline form of the disclosure is administered in an amount effective to treat a condition as described herein, and can be administered as crystalline compound per se, or alternatively, as a pharmaceutically acceptable salt. For administration and dosing purposes, the crystalline compound per se or pharmaceutically acceptable salt thereof will simply be referred to as the compounds of the disclosure.

The compounds of the disclosure are administered by any suitable route in the form of a pharmaceutical composition adapted to such a route, and in a dose effective for the treatment intended. The compounds of the disclosure may be administered orally, rectally, vaginally, parenterally, or topically.

The compounds of the disclosure may be administered orally. Oral administration may involve swallowing, so that the compound enters the gastrointestinal tract, or buccal or sublingual administration may be employed by which the compound enters the bloodstream directly from the mouth.

In another embodiment, the compounds of the disclosure may also be administered directly into the bloodstream, into muscle, or into an internal organ. Suitable means for parenteral administration include intravenous, intraarterial, intraperitoneal, intrathecal, intraventricular, intraurethral, intrasternal, intracranial, intramuscular and subcutaneous. Suitable devices for parenteral administration include needle (including microneedle) injectors, needle-free injectors and infusion techniques.

In another embodiment, the compounds of the disclosure may also be administered topically to the skin or mucosa, that is, dermally or transdermally. In another embodiment, the compounds of the disclosure can also be administered intranasally or by inhalation. In another embodiment, the compounds of the disclosure may be administered rectally or vaginally. In another embodiment, the compounds of the disclosure may also be administered directly to the eye or ear.

The dosage regimen for the compounds of the disclosure and/or compositions containing said compounds is based on a variety of factors, including the type, age, weight, sex and medical condition of the patient; the severity of the condition; the route of administration; and the activity of the particular compound employed. Thus, the dosage regimen may vary widely. In one embodiment, the total daily dose of a compound of the disclosure is typically from about 0.01 to about 100 mg/kg (i.e., mg compound of the disclosure per kg body weight) for the treatment of the indicated conditions discussed herein. In another embodiment, total daily dose of the compound of the disclosure is from about 0.1 to about 50 mg/kg, and in another embodiment, from about 0.5 to about 30 mg/kg.

For oral administration, the compositions may be provided in the form of tablets containing 0.01, 0.05, 0.1, 0.5, 1.0, 2.5, 5.0, 10.0, 15.0, 25.0, 50.0, 75.0, 100, 125, 150, 175, 200, 250 and 500 milligrams of the active ingredient for the symptomatic adjustment of the dosage to the patient. A medicament typically contains from about 0.01 mg to about 500 mg of the active ingredient, or in another embodiment, from about 1 mg to about 100 mg of active ingredient. Intravenously, doses may range from about 0.01 to about 10 mg/kg/minute during a constant rate infusion.

Suitable subjects according to the disclosure include mammalian subjects. Mammals according to the disclosure include canine, feline, bovine, caprine, equine, ovine, porcine, rodents, lagomorphs, primates, and the like, and encompass mammals in utero. In one embodiment, humans are suitable subjects. Human subjects may be of either gender and at any stage of development.

In another embodiment, the disclosure comprises pharmaceutical compositions. Such pharmaceutical compositions comprise a compound of the disclosure presented with a pharmaceutically acceptable carrier. Other pharmacologically active substances can also be present. As used herein, "pharmaceutically acceptable carrier" includes any and all solvents, dispersion media, coatings, antibacterial and antifungal agents, isotonic and absorption delaying agents, and the like that are physiologically compatible. Examples of pharmaceutically acceptable carriers include one or more of water, saline, phosphate buffered saline, dextrose, glycerol, ethanol and the like, as well as combinations thereof, and may include isotonic agents, for example, sugars, sodium chloride, or polyalcohols such as mannitol, or sorbitol in the composition. Pharmaceutically acceptable substances such as wetting agents or minor amounts of auxiliary substances such as wetting or emulsifying agents, preservatives or buffers, which enhance the shelf life or effectiveness of the antibody or antibody portion.

The compositions of this disclosure may be in a variety of forms. These include, for example, liquid, semi-solid and solid dosage forms, such as liquid solutions (e.g., injectable and infusible solutions), dispersions or suspensions, tablets, pills, powders, liposomes and suppositories. The form depends on the intended mode of administration and therapeutic application.

Typical compositions are in the form of injectable or infusible solutions, such as compositions similar to those used for passive immunization of humans with antibodies in general. One mode of administration is parenteral (e.g., intravenous, subcutaneous, intraperitoneal, intramuscular). In another embodiment, the antibody is administered by intravenous infusion or injection. In yet another embodiment, the antibody is administered by intramuscular or subcutaneous injection.

Oral administration of a solid dose form may be, for example, presented in discrete units, such as hard or soft capsules, pills, cachets, lozenges, or tablets, each containing a predetermined amount of at least one compound of the disclosure. In another embodiment, the oral administration may be in a powder or granule form. In another embodiment, the oral dose form is sub-lingual, such as, for example, a lozenge. In such solid dosage forms, the crystalline compound is ordinarily combined with one or more adjuvants. Such capsules or tablets may contain a controlled release formulation. In the case of capsules, tablets, and pills, the dosage forms also may comprise buffering agents or may be prepared with enteric coatings.

In another embodiment, oral administration may be in a liquid dose form. Liquid dosage forms for oral administration include, for example, pharmaceutically acceptable emulsions, solutions, suspensions, syrups, and elixirs containing inert diluents commonly used in the art (e.g., water). Such compositions also may comprise adjuvants, such as wetting, emulsifying, suspending, flavoring (e.g., sweetening), and/or perfuming agents.

In another embodiment, the disclosure comprises a parenteral dose form. "Parenteral administration" includes, for example, subcutaneous injections, intravenous injections, intraperitoneally, intramuscular injections, intrasternal injections, and infusion. Injectable preparations (i.e., sterile injectable aqueous or oleaginous suspensions) may be formulated according to the known art using suitable dispersing, wetting agents, and/or suspending agents.

In another embodiment, the disclosure comprises a topical dose form. "Topical administration" includes, for example, transdermal administration, such as via transdermal patches or iontophoresis devices, intraocular administration, or intranasal or inhalation administration. Compositions for topical administration also include, for example, topical gels, sprays, ointments, and creams. A topical formulation may include a crystalline compound which enhances absorption or penetration of the active ingredient through the skin or other affected areas. When the crystalline compound of this disclosure is administered by a transdermal device, administration will be accomplished using a patch either of the reservoir and porous membrane type or of a solid matrix variety. Typical formulations for this purpose include gels, hydrogels, lotions, solutions, creams, ointments, dusting powders, dressings, foams, films, skin patches, wafers, implants, sponges, fibers, bandages and microemulsions. Liposomes may also be used. Typical carriers include alcohol, water, mineral oil, liquid petrolatum, white petrolatum, glycerin, polyethylene glycol and propylene glycol. Penetration enhancers may be incorporated—see, for example, B. C. Finnin and T. M. Morgan, J. Pharm. Sci., vol. 88, pp. 955-958, 1999.

Accordingly, topical formulations of the presently disclosed crystalline form of (1R,3R)-3-(cyanomethyl)-3-(4-(6-(1-methyl-1H-pyrazol-4-yl)pyrazolo[1,5-a]pyrazin-4-yl)-1H-pyrazol-1-yl)cyclobutane-1-carbonitrile may be administered using such preparations encompassing all conventional methods of administration across the surface of the body and the inner linings of body passages including epithelial and mucosal tissues, including transdermal, epidermal, buccal, pulmonary, ophthalmic, intranasal, vaginal and rectal modes of administration. Typical carriers include alcohol, water, mineral oil, liquid petrolatum, white petrolatum, glycerin, polyethylene glycol and propylene glycol.

Such topical formulations may be prepared in combination with additional pharmaceutically acceptable excipients. An excipient which may be essential to clinical efficacy is one or more penetration enhancer such as be one or more saturated or cis-unsaturated C10-C18 fatty alcohols. Such fatty alcohols include C16-C18 fatty alcohols, and most preferably, are a C18 fatty alcohol. Examples of cis-unsaturated C16-C18 fatty alcohols include oleyl alcohol, linoleyl alcohol, γ-linolenyl alcohol and linolenyl alcohol. Saturated C10-C18 fatty alcohols useful as penetration enhancers include decyl alcohol, lauryl alcohol, myristyl alcohol, cetyl alcohol and stearyl alcohol. Alternatively, other penetration enhancers which may be used to prepare the topical formulations include C10-C18 fatty acids, which when saturated may include capric acid, lauric acid, myristic acid, palmitic acid, stearic acid and arachidic acid. Alternatively, the penetration enhancer may usefully be a cis-unsaturated fatty acid, such as palmitoleic acid (cis-9-hexadecenoic acid), oleic acid (cis-9-octadecenoic acid), cis-vaccenic acid (cis-11-octadecenoic acid), linoleic acid (cis-9,12-octadecadienoic acid), γ-linolenic acid (cis-6,9,12-octadecatrienoic acid), linolenic acid (cis-9,12,15-octadecatrienoic acid) and arachidonic acid (cis-5,8,11,14-eicosatetraenoic acid). The penetration enhancers, for example, one selected from C10-C18 fatty alcohols, are used in amounts ranging from about 0.1 to about 5% (w/v), more preferably, from 1 to about 4%, more preferably still, 1 to about 3% (w/v).

Topical formulations contain (1R,3R)-3-(cyanomethyl)-3-(4-(6-(1-methyl-1H-pyrazol-4-yl)pyrazolo[1,5-a]pyrazin-4-yl)-1H-pyrazol-1-yl)cyclobutane-1-carbonitrile in therapeutically effective amounts that can be given in daily or twice daily doses to patients in need. These amounts range from about 0.1% to about 5.0% (w/v), more preferably, from about 0.1% to about 3.0% (w/v). Among other excipients which enhance the stability of these formulations include aldehyde scavengers, such as glycerine and propylene glycol, and antioxidants, such as butyl hydroxyanisole (BHA), butyl hydroxytoluene (BHT), propyl gallate, ascorbic acid (Vitamin C), polyphenols, tocopherols (Vitamin E), and their derivatives.

Formulations suitable for topical administration to the eye include, for example, eye drops wherein the compound of this disclosure is dissolved or suspended in a suitable carrier. A typical formulation suitable for ocular or aural administration may be in the form of drops of a micronized suspension or solution in isotonic, pH-adjusted, sterile saline. Other formulations suitable for ocular and aural administration include ointments, biodegradable (i.e., absorbable gel sponges, collagen) and non-biodegradable (i.e., silicone) implants, wafers, lenses and particulate or vesicular systems, such as niosomes or liposomes. A polymer such as crossed linked polyacrylic acid, polyvinyl alcohol, hyaluronic acid, a cellulosic polymer, for example, hydroxypropylmethylcellulose, hydroxyethylcellulose, or methylcellulose, or a heteropolysaccharide polymer, for example, gelan gum, may be incorporated together with a preservative, such as benzalkonium chloride. Such formulations may also be delivered by iontophoresis.

For intranasal administration or administration by inhalation, the crystalline compound of the disclosure is conveniently delivered in the form of a solution or suspension from a pump spray container that is squeezed or pumped by the patient or as an aerosol spray presentation from a pressurized container or a nebulizer, with the use of a suitable propellant. Formulations suitable for intranasal administration are typically administered in the form of a dry powder (either alone, as a mixture, for example, in a dry blend with lactose, or as a mixed component particle, for example, mixed with phospholipids, such as phosphatidylcholine) from a dry powder inhaler or as an aerosol spray from a pressurized container, pump, spray, atomizer (preferably an atomizer using electrohydrodynamics to produce a fine mist), or nebulizer, with or without the use of a suitable propellant, such as 1,1,1,2-tetrafluoroethane or 1,1,1,2,3,3,3-heptafluoropropane. For intranasal use, the powder may comprise a bioadhesive agent, for example, chitosan or cyclodextrin.

In another embodiment, the disclosure comprises a rectal dose form. Such rectal dose form may be in the form of, for example, a suppository. Cocoa butter is a traditional suppository base, but various alternatives may be used as appropriate.

Other carrier materials and modes of administration known in the pharmaceutical art may also be used. Pharmaceutical compositions of the disclosure may be prepared by any of the well-known techniques of pharmacy, such as effective formulation and administration procedures. The above considerations in regard to effective formulations and administration procedures are well known in the art and are described in standard textbooks. Formulation of drugs is discussed in, for example, Hoover, John E., Remington's Pharmaceutical Sciences, Mack Publishing Co., Easton, Pennsylvania, 1975; Liberman et al., Eds., Pharmaceutical Dosage Forms, Marcel Decker, New York, N.Y., 1980; and Kibbe et al., Eds., Handbook of Pharmaceutical Excipients (3rd Ed.), American Pharmaceutical Association, Washington, 1999.

The crystalline compound of the disclosure can be used alone, or in combination with other therapeutic agents. The disclosure provides any of the uses, methods or compositions as defined herein wherein the crystalline compound herein, or pharmaceutically acceptable solvate of said compound, is used in combination with one or more other therapeutic agent discussed herein.

The administration of two or more compounds "in combination" means that all of the compounds are administered closely enough in time that the presence of one alters the biological effects of any other compound(s). The two or more compounds may be administered simultaneously, concurrently or sequentially. Additionally, simultaneous administration may be carried out by mixing the compounds prior to administration or by administering the compounds at the same point in time but as separate dosage forms at the same or different site of administration.

The phrases "concurrent administration," "co-administration," "simultaneous administration," and "administered simultaneously" mean that the compounds are administered in combination.

In another embodiment, the disclosure provides methods of treatment that include administering the crystalline compound of the disclosure in combination with one or more other pharmaceutical agents, wherein the one or more other pharmaceutical agents may be selected from the agents discussed herein.

These agents and the crystalline compound of the disclosure can be combined with pharmaceutically acceptable vehicles such as saline, Ringer's solution, dextrose solution, and the like. The particular dosage regimen, i.e., dose, timing and repetition, will depend on the particular individual and that individual's medical history.

Acceptable carriers, excipients, or stabilizers are nontoxic to recipients at the dosages and concentrations employed, and may comprise buffers such as phosphate, citrate, and other organic acids; salts such as sodium chloride; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens, such as methyl or propyl paraben; catechol; resorcinol; cyclohexanol; 3-pentanol; and m-cresol); low molecular weight (less than about 10 residues) polypeptides; proteins, such as serum albumin, gelatin, or Igs; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN™, PLURONICS™ or polyethylene glycol (PEG).

Liposomes containing these agents and/or compounds of the disclosure are prepared by methods known in the art, such as described in U.S. Pat. Nos. 4,485,045 and 4,544,545. Liposomes with enhanced circulation time are disclosed in U.S. Pat. No. 5,013,556. Particularly useful liposomes can be generated by the reverse phase evaporation method with a lipid composition comprising phosphatidylcholine, cholesterol and PEG-derivatized phosphatidylethanolamine (PEG-PE). Liposomes are extruded through filters of defined pore size to yield liposomes with the desired diameter.

These agents and/or the compounds of the disclosure may also be entrapped in microcapsules prepared, for example, by coacervation techniques or by interfacial polymerization, for example, hydroxymethylcellulose or gelatin-microcapsules and poly-(methylmethacrylate) microcapsules, respectively, in colloidal drug delivery systems (for example, liposomes, albumin microspheres, microemulsions, nanoparticles and nanocapsules) or in macroemulsions. Such techniques are disclosed in Remington, The Science and Practice of Pharmacy, 20th Ed., Mack Publishing (2000).

Sustained-release preparations may be used. Suitable examples of sustained-release preparations include semipermeable matrices of solid hydrophobic polymers containing the antibody/compound of the disclosure, which matrices are in the form of shaped articles, e.g., films, or microcapsules. Examples of sustained-release matrices include polyesters, hydrogels (for example, poly(2-hydroxyethyl-methacrylate), or 'poly(vinylalcohol)), polylactides (U.S. Pat. No. 3,773,919), copolymers of L-glutamic acid and 7 ethyl-L-glutamate, non-degradable ethylene-vinyl acetate, degradable lactic acid-glycolic acid copolymers such as those used in LUPRON DEPOT™ (injectable microspheres composed of lactic acid-glycolic acid copolymer and leuprolide acetate), sucrose acetate isobutyrate, and poly-D-(−)-3-hydroxybutyric acid.

The formulations to be used for intravenous administration must be sterile. This is readily accomplished by, for example, filtration through sterile filtration membranes. Crystalline compound of the disclosure is generally placed into a container having a sterile access port, for example, an intravenous solution bag or vial having a stopper pierceable by a hypodermic injection needle.

Suitable emulsions may be prepared using commercially available fat emulsions, such as Intralipid™, Liposyn™, Infonutrol™, Lipofundin™ and Lipiphysan™. The active ingredient may be either dissolved in a pre-mixed emulsion composition or alternatively it may be dissolved in an oil (e.g., soybean oil, safflower oil, cottonseed oil, sesame oil, corn oil or almond oil) and an emulsion formed upon mixing with a phospholipid (e.g., egg phospholipids, soybean phospholipids or soybean lecithin) and water. It will be appreciated that other ingredients may be added, for example glycerol or glucose, to adjust the tonicity of the emulsion. Suitable emulsions will typically contain up to 20% oil, for example, between 5 and 20%. The fat emulsion can comprise fat droplets between 0.1 and 1.0 µm, particularly 0.1 and 0.5 µm, and have a pH in the range of 5.5 to 8.0.

The compounds of these teachings can be prepared by methods known in the art. The reagents used in the preparation of the compounds of these teachings can be either commercially obtained or can be prepared by standard procedures described in the literature. For example, compounds of the present disclosure can be prepared according to the methods illustrated in the following examples.

The description of this disclosure utilizes a variety of abbreviations well known to those skilled in the art, including the following:

aq.: aqueous
$CH_3CN$: Acetonitrile
DCM: Dichloromethane
DMF: N,N-Dimethylformamide
DMSO: Dimethylsulfoxide
EtOAc: Ethyl acetate
EtOH: Ethanol
FT-IR: Fourier Transform-Infrared
HOAc: Acetic acid
MeOH: Methanol
PXRD: powder X-ray diffraction
ss $^{13}C$ NMR: solid state $^{13}C$ nuclear magnetic resonance
THF: Tetrahydrofuran
TLC: Thin Layer Chromatography

EXAMPLES

The following non-limiting example is presented merely to illustrate the present disclosure. The skilled person will understand that there are numerous equivalents and variations not exemplified but which still form part of the present teachings.

Example 1

Preparation of (1R,3R)-3-(cyanomethyl)-3-(4-(6-(1-methyl-1H-pyrazol-4-yl)pyrazolo[1,5-a]pyrazin-4-yl)-1H-pyrazol-1-yl)cyclobutane-1-carbonitrile Form 2—Monohydrate Recrystallization was effected by suspending the anhydrous (1R,3R)-3-(cyanomethyl)-3-(4-(6-(1-methyl-1H-pyrazol-4-yl)pyrazolo[1,5-a]pyrazin-4-yl)-1H-pyrazol-1-yl)cyclobutane-1-carbonitrile Form 1 (20 g) in THF (595 mL), methanol (70 mL) and water (35 mL) at 20 to 30° C. The mixture was heated under reflux for 30 min. The resulting solution was transferred to a preheated (65° C.) vessel through a HALAR® filter followed by a wash with preheated THF-methanol-water (85-10-05% v/v/v) mixture (spec free operation). The sample was stirred for 30 min before the mixture was cooled to 5° C. for 4.5 h before being transferred to a filter drier and washed with cold (5° C.) THF-water mixture 95-05% v/v. The precipitate was dried at room temperature (under humidified conditions) until the THF residue was <0.02%, affording Form 2 monohydrate as a white, free flowing powder.

Example 2

Preparation of Anhydrous Free Base (1R,3R)-3-(cyanomethyl)-3-(4-(6-(1-methyl-1H-pyrazol-4-yl)pyrazolo[1,5-a]pyrazin-4-yl)-1H-pyrazol-1-yl)cyclobutane-1-carbonitrile, Form 1

Recrystallization was effected by suspending the anhydrous (1R,3R)-3-(cyanomethyl)-3-(4-(6-(1-methyl-1H-pyrazol-4-yl)pyrazolo[1,5-a]pyrazin-4-yl)-1H-pyrazol-1-yl)cyclobut-ane-1-carbonitrile Form 2 monohydrate (20 g) in THF (595 mL), methanol (70 mL) and water (35 mL) at 20 to 30° C. The mixture was heated under reflux for 30 min. The resulting solution was transferred to a preheated (65° C.) vessel through a HALAR® filter and followed by a wash with preheated THF-methanol-Water (85-10-05% v/v/v) mixture (spec free operation). The sample was stirred for 30 minutes before cooling back to 50° C. The sample was then distilled under partial vacuum by controlling the jacket temperature between 50° C. to 70° C.). The final volume of ~15 mL/g was achieved by distillation. To the sample was added 15 mL/g of ethyl acetate (300 mL). The sample was again distilled to match the final volume to 15 mL/g after distillation. The same operation was repeated 2 times to remove THF, methanol and water (Limit: NMT 2 wt % of THF and methanol and NMT 0.5 wt % of water). The sample was stirred for 30 min before the mixture was cooled to 20° C. for 4.5 h before being transferred to a filter drier and washed with ethyl acetate 3 mL/g. The precipitate was dried at 50° C. temperature until the ethyl acetate residue was <0.02% to afford Form 1 anhydrous free base as a white, free flowing powder.

Example 3

Preparation of (1R,3R)-3-(cyanomethyl)-3-(4-(6-(1-methyl-1H-pyrazol-4-yl)pyrazolo[1,5-a]pyrazin-4-yl)-1H-pyrazol-1-yl)cyclobutane-1-carbonitrile, Form 2—Monohydrate 4-Chloro-6-(1-methyl-1H-pyrazol-4-yl)pyrazolo[1,5-a]pyrazine (2.0 g, 8.6 mmol, 100 mass %) and (1r,3r)-3-(cyanomethyl)-3-(4-(4,4,5,5-tetramethyl-1,3,2-dioxaborolan-2-yl)-1H-pyrazol-1-yl)cyclobutane-1-carbonitrile (2.8 g, 9.0 mmol, 100 mass %) were combined in the presence of sodium bicarbonate (1.40 g, 16.7 mmol, 100 mass %) in THF (22 mL) and water (24 mL). The mixture was heated to 35° C. for 5 minutes. In a separate container chloro(2-dicyclohexylphosphino-2',4',6'-triisopropyl-1,1'-biphenyl)[2-(2'-amino-1,1'-biphenyl)]palladium(II) (14 mg, 0.01744 mmol, 98 mass %) was charged and degassed using nitrogen followed by the catalyst charge in THF. The catalyst solution was then added to the reaction mixture at 35° C., which was then heated to 65° C. for 2 hours. 1,2-bis(Diphenylphosphino)ethane (20 mg, 0.05020 mmol, 100 mass %) in 1 mL of tetrahydrofuran was added, and the reaction mixture was stirred for 60 minutes at 65° C. The sample was then cooled to 20° C. and stirred for 90 minutes. Solids were filtered, and the filter cake was then again placed in the reactor and re-slurried in water. The slurry was transferred to a filter drier and washed with water. The solids were dried at room temperature (under humidified conditions) until the THF residue was <0.02% to afford Form 2 monohydrate as a white, free flowing powder.

Instrument and Analysis Methods:
Powder X-Ray Diffraction (PXRD)

PXRD patterns of the API were collected on a Bruker D8 Endeavour powder X-ray diffractometer fitted with an automatic sample changer, a theta-2theta goniometer and a Lynxeye XE-T detector with a PSD window size of 4.00°. Primary motorized slits set at constant illumination of 11.0 mm, anti-scattering slits set at constant distance of 2.20 mm. The X-ray tube voltage and amperage were set to 40 kV and 40 mA respectively. Data was collected at the Cu wavelength using a step size of 0.019 degrees and scan time of 10 minutes scanning from 2.0 to 55.0 degrees 2θ. The sample was prepared by placing the powder in a Si low background cavity holder. The sample powder was pressed by a glass slide to ensure that a proper sample height was achieved. Data were collected using Bruker DIFFRAC software and analysis was performed by DIFFRAC EVA software. The PXRD patterns collected were imported into Bruker DIFFRAC EVA software. The peak selection was carried out utilizing the software's "peak search function" and then was carefully checked and corrected to ensure that all peak positions had been accurately assigned. Peaks were catalogued between 2 and 32° 2θ. A typical error of ±0.2° 2θ in peak positions applies to this data. The minor error associated with this measurement can occur because of a variety of factors including: (a) sample preparation (e.g., sample height), (b) instrument, (c) calibration, (d) operator (including those errors present when determining the peak locations), and (e) the nature of the material (e.g., preferred orientation and transparency errors). Therefore, peaks are considered to have a typical associated error of ±0.2° 2θ. When two peaks, in the list, are considered to overlap the less intense peak has been removed from the listing. Peaks existing as shoulders, on a higher intensity adjacent peak, have also been removed from the peak list. While the shoulders may be >0.2° 2θ from the position of the adjacent peak, they are not considered as discernible from the adjacent peak. To obtain the absolute peak positions, the powder pattern should be aligned against a reference. This could either be the simulated powder pattern from the crystal structure of the same form solved at room temperature, or an internal standard, e.g., silica or corundum. Simulated powder patterns of (1R,3R)-3-(cyanomethyl)-3-(4-(6-(1-methyl-1H-pyrazol-4-yl)pyrazolo[1,5-a]pyrazin-4-yl)-1H-pyrazol-1-yl)cyclobutane-1-carbonitrile Form 1 and Form 2 were obtained from single crystal structures. A simulated powder pattern from the single crystal structure was obtained via a calculation using Mercury 4.1.0 which is part of the CCDC 5.40 Software Suite. PXRD Reflection Assignments: Peak values were assigned at the maximum intensity of a given reflection.

The PXRD profile for (1R,3R)-(cyanomethyl)-3-(4-(6-(1-methyl-1H-pyrazol-4-yl)pyrazolo[1,5-a]pyrazin-4-yl)-1H-pyrazol-1-yl)cyclobut-ane-1-carbonitrile Form 1 anhydrous free base is provided in FIG. 1. A peak list is included in Table 1. Several peaks were selected as characteristic peaks for (1R,3R)-3-(cyanomethyl)-3-(4-(6-(1-methyl-1H-pyrazol-4-yl)pyrazolo[1,5-a]pyrazin-4-yl)-1H-pyrazol-1-yl)cyclobutane-1-carb-onitrile Form 1 anhydrous free base. The PXRD profile for (1R,3R)-3-(cyanomethyl)-3-(4-(6-(1-methyl-1H-pyrazol-4-yl)pyrazolo[1,5-a]pyrazin-4-yl)-1H-pyrazol-1-yl)cyclobutane-1-carbonitrile Form 2 monohydrate is provided in FIG. 2. A peak list is included in Table 2. Several peaks were selected as characteristic for (1R,3R)-3-(cyanomethyl)-3-(4-(6-(1-methyl-1H-pyrazol-4-yl)pyrazolo[1,5-a]pyrazin-4-yl)-1H-pyrazol-1-yl)cyclobutane-1-carb-onitrile Form 2 monohydrate.

TABLE 1

PXRD peak list for (1R,3R)-3-(cyanomethyl)-3-(4-(6-(1-methyl-1H-pyrazol-4-yl)pyrazolo[1,5-a]pyrazin-4-yl)-1H-pyrazol-1-yl)cyclobutane-1-carbonitrile, Form 1 anhydrous free base. Asterisked peaks are characteristic for Form 1, anhydrous free base.

| °2θ ± 0.2 °2θ | % Relative Intensity |
|---|---|
| 8.1 | 6.0* |
| 8.9 | 21.7 |
| 11.0 | 72.0 |
| 12.1 | 1.2 |
| 12.5 | 15.8 |
| 12.9 | 2.9 |
| 14.1 | 45.8 |
| 14.9 | 7.4 |
| 16.2 | 35.6 |
| 17.3 | 18.7 |
| 17.6 | 28.1 |
| 18.0 | 25.3* |
| 18.4 | 16.2 |
| 19.6 | 9.5 |
| 20.6 | 36.8* |
| 21.5 | 15.2 |
| 22.2 | 75.6 |
| 22.8 | 43.8* |
| 23.2 | 38.6 |
| 23.7 | 13.1 |
| 24.0 | 5.6 |
| 24.3 | 27.0 |
| 25.0 | 15.9 |
| 25.9 | 21.8 |
| 27.0 | 100.0* |
| 27.7 | 71.9 |
| 29.1 | 6.5 |
| 29.8 | 3.2 |
| 30.2 | 9.9 |
| 30.5 | 16.0 |
| 31.1 | 8.1 |

Five characteristic peaks recommended as diagnostic peaks for (1R,3R)-3-(cyanomethyl)-3-(4-(6-(1-methyl-1H-pyrazol-4-yl)pyrazolo[1,5-a]pyrazin-4-yl)-1H-pyrazol-1-yl)cyclobutane-1-carbonitrile Form 1 anhydrous, at 8.1°, 18.0°, 20.6°, 22.8° and 27.0° 2θ.

TABLE 2

PXRD peak list for (1R,3R)-3-(cyanomethyl)-3-(4-(6-(1-methyl-1H-pyrazol-4-yl)pyrazolo[1,5-a]pyrazin-4-yl)-1H-pyrazol-1-yl)cyclobutane-1-carbonitrile, Form 2 Monohydrate.

| °2θ ± 0.2 °2θ | % Relative Intensity |
|---|---|
| 7.4 | 44.2* |
| 8.8 | 86.5 |
| 10.4 | 5.3* |
| 11.1 | 4.4 |
| 12.4 | 42.6 |
| 12.8 | 1.0 |
| 13.8 | 13.0 |
| 14.0 | 5.4 |
| 14.3 | 0.7 |
| 14.9 | 18.8 |
| 15.7 | 11.9* |
| 16.2 | 74.7 |
| 17.2 | 1.3 |
| 17.5 | 3.4 |
| 18.5 | 20.3 |
| 18.7 | 8.9 |
| 19.2 | 3.6 |
| 19.9 | 8.5 |
| 20.2 | 7.4 |
| 20.9 | 26.0 |
| 22.3 | 38.8 |
| 23.0 | 1.2 |

TABLE 2-continued

PXRD peak list for (1R,3R)-3-(cyanomethyl)-3-(4-(6-(1-methyl-1H-pyrazol-4-yl)pyrazolo[1,5-a]pyrazin-4-yl)-1H-pyrazol-1-yl)cyclobutane-1-carbonitrile, Form 2 Monohydrate.

| °2θ ± 0.2 °2θ | % Relative Intensity |
|---|---|
| 23.2 | 1.9 |
| 23.6 | 3.9 |
| 24.0 | 67.0 |
| 25.0 | 24.8 |
| 25.7 | 40.5 |
| 26.2 | 100.0* |
| 26.8 | 2.1 |
| 27.8 | 93.7 |
| 28.5 | 36.1* |
| 30.1 | 35.5 |
| 30.6 | 3.0 |
| 30.9 | 6.4 |
| 31.3 | 2.2 |
| 31.8 | 1.7 |

Five characteristic peaks are recommended as diagnostic peaks for Form 2 monohydrate at 7.4°, 10.4°, 15.7°, 26.2°, 28.5° 2θ.

Solid State NMR: Solid state NMR (ssNMR) analysis was conducted on a CPMAS probe positioned into a Bruker-BioSpin Avance III™ 500 MHz ($^1$H frequency) NMR spectrometer. Material was packed into a 4 mm rotor sealed with a standard drive cap. A magic angle spinning rate of 15.0 kHz was used. A phase modulated proton decoupling field of 80-90 kHz was applied during spectral acquisition. $^{13}$C ssNMR spectrum was collected using a proton decoupled cross-polarization magic angle spinning (CPMAS) experiment. The cross-polarization contact time was set to 3 ms and the recycle delay to 60 seconds. The number of scans was adjusted to obtain an adequate signal to noise ratio, with 768 scans being collected for the API and more scans, typically >4096, being collected for a drug product. The $^{13}$C chemical shift scale was referenced using a $^{13}$C CPMAS experiment on an external standard of crystalline adamantane, setting its up-field resonance to 29.5 ppm.

Automatic peak picking was performed using Bruker-BioSpin TopSpin™ version 3.5 software. Generally, a threshold value of 5% relative intensity was used for preliminary peak selection. The output of the automated peak picking was visually checked to ensure validity and adjustments were manually made if necessary. Although specific solid state NMR peak values are reported herein there does exist a range for these peak values due to differences in instruments, samples, and sample preparation. The solid state NMR peak heights reported herein are relative intensities. Solid state NMR intensities can vary depending on the actual setup of the CPMAS experimental parameters and the thermal history of the sample. Intensities can vary depending on the actual setup of the CPMAS experimental parameters and the thermal history of the sample. CPMAS intensities are not necessarily quantitative.

$^{13}$C solid state NMR peak lists for the crystalline forms (1R,3R)-3-(cyanomethyl)-3-(4-(6-(1-methyl-1H-pyrazol-4-yl)pyrazolo[1,5-a]pyrazin-4-yl)-1H-pyrazol-1-yl)cyclobutane-1-carbonitrile, Form 1 anhydrous and Form 2 monohydrate are shown respectively in Tables 3 and 4.

TABLE 3

$^{13}$C solid state NMR peak list for (1R,3R)-3-(cyanomethyl)-3-(4-(6-(1-methyl-1H-pyrazol-4-yl)pyrazolo[1,5-a]pyrazin-4-yl)-1H-pyrazol-1-yl)cyclobutane-1-carbonitrile, Form 1 anhydrous.

| δ/ppm | Rel. Intensity, % |
|---|---|
| 15.2 | 45.8 |
| 32.1 | 40.3 |
| 33.1 | 38.5 |
| 35.2 | 36.3 |
| 42.4 | 50.2 |
| 60.2 | 70.1 |
| 98.2 | 35.7 |
| 114.2 | 33.2 |
| 118.0 | 12.0 |
| 120.5 | 68.6 |
| 121.2 | 68.3 |
| 123.3 | 12.7 |
| 124.7 | 22.5 |
| 128.3 | 34.7 |
| 131.4 | 100.0 |
| 138.5 | 51.3 |
| 143.5 | 74.8 |

Resonances at 131.4, 60.2, 143.5, 121.2 and 120.5 ppm are characteristic peaks for Form 1 anhydrous.

TABLE 4

$^{13}$C solid state NMR peak list for (1R,3R)-3-(cyanomethyl)-3-(4-(6-(1-methyl-1H-pyrazol-4-yl)pyrazolo[1,5-a]pyrazin-4-yl)-1H-pyrazol-1-yl)cyclobutane-1-carbonitrile, Form 2 monohydrate.

| δ/ppm | Rel. Intensity, % |
|---|---|
| 15.4 | 42.9 |
| 30.6 | 30.3 |
| 36.5 | 53.8 |
| 40.0 | 47.0 |
| 61.8 | 61.9 |
| 96.3 | 36.7 |
| 113.9 | 34.7 |
| 120.8 | 100.0 |
| 123.3 | 23.4 |
| 125.7 | 33.2 |
| 130.9 | 57.7 |
| 133.2 | 47.9 |
| 138.3 | 38.5 |
| 142.8 | 54.1 |

Resonances at 130.9, 120.8, 142.8, 40.0 and 61.8 ppm are characteristic peaks for Form 2 monohydrate.

FT-Raman Spectroscopy

Raman spectra were collected using a RAM II FT-Raman module attached to a Vertex 70 FTIR spectrometer (Bruker Optik GmbH). The instrument is equipped with a 1064 nm solid-state (Nd:YAG) laser and a liquid nitrogen cooled germanium detector. Prior to data acquisition, instrument performance and calibration verifications were conducted using a white light source, and polystyrene and naphthalene references. Raman spectral peaks for the crystalline form are shown in Table 2. Samples were prepared and analyzed in truncated NMR tubes. A sample rotator (Ventacon, UK) was used during measurement to maximize the volume of material exposed to the laser during data collection. The backscattered Raman signal from the sample was optimized and data were collected at a spectral resolution of 2 cm-1 using a laser power of 500 mW. A Blackmann-Harris 4-term apodization function was applied to minimize spectral aberrations. Spectra were generated between 3500 and 50 cm-1 with the number of scans adjusted accordingly to ensure adequate signal to noise. Spectra were normalized by setting the intensity of the most intense peak to 2.00. Peaks were then identified using the automatic peak picking function in the OPUS v8.2 software (Bruker Optik GmbH) with the sensitivity set to 2%. Peak positions and relative peak intensities were extracted and tabulated. The variability in the peak positions with this experimental configuration is within ±2 cm$^{-1}$. It is expected that, since FT-Raman and dispersive Raman are similar techniques, peak positions reported in this document for FT-Raman spectra would be consistent with those which would be observed using a dispersive Raman measurement, assuming appropriate instrument calibration.

TABLE 5

Full Raman peak list for (1R,3R)-3-(cyanomethyl)-3-(4-(6-(1-methyl-1H-pyrazol-4-yl)pyrazolo[1,5-a]pyrazin-4-yl)-1H-pyrazol-1-yl)cyclobutane-1-carbonitrile, Form 1.

| Wavenumber (cm−1) | Relative Intensity (%) |
|---|---|
| 439 | 3.5 |
| 525 | 4.4 |
| 663 | 3.9 |
| 688 | 2.3 |
| 826 | 2.3 |
| 845 | 14.0 |
| 924 | 16.2 |
| 965 | 8.1 |
| 988 | 4.6 |
| 1002 | 5.7 |
| 1016 | 4.7 |
| 1079 | 5.6 |
| 1137 | 13.1 |
| 1157 | 3.0 |
| 1190 | 8.2 |
| 1206 | 7.0 |
| 1224 | 12.3 |
| 1246 | 24.0 |
| 1277 | 7.3 |
| 1293 | 12.5 |
| 1306 | 5.0 |
| 1322 | 7.2 |
| 1353 | 26.6 |
| 1377 | 12.3 |
| 1422 | 14.8 |
| 1443 | 22.6 |
| 1498 | 54.9 |
| 1564 | 100.0 |
| 1619 | 55.2 |
| 2242 | 21.3 |
| 2923 | 7.3 |
| 2971 | 18.8 |
| 3019 | 3.1 |
| 3105 | 10.5 |
| 3144 | 4.7 |

1498, 2923, 1246, 1443 and 2971 cm$^{-1}$ were chosen as characteristic peaks for Form 1 anhydrous.

TABLE 6

Full Raman peak list for (1R,3R)-3-(cyanomethyl)-3-(4-(6-(1-methyl-1H-pyrazol-4-yl)pyrazolo[1,5-a]pyrazin-4-yl)-1H-pyrazol-1-yl)cyclobutane-1-carbonitrile, Form 2.

| Wavenumber (cm−1) | Relative Intensity (%) |
|---|---|
| 431 | 5.3 |
| 495 | 2.6 |
| 531 | 7.3 |
| 643 | 4.1 |
| 687 | 3.2 |
| 706 | 3.7 |
| 767 | 3.6 |
| 848 | 11.8 |

TABLE 6-continued

Full Raman peak list for (1R,3R)-3-(cyanomethyl)-3-(4-(6-(1-methyl-1H-pyrazol-4-yl)pyrazolo[1,5-a]pyrazin-4-yl)-1H-pyrazol-1-yl)cyclobutane-1-carbonitrile, Form 2.

| Wavenumber (cm−1) | Relative Intensity (%) |
|---|---|
| 882 | 4.6 |
| 915 | 2.9 |
| 930 | 12.4 |
| 967 | 4.1 |
| 981 | 5.9 |
| 994 | 2.6 |
| 1001 | 8.3 |
| 1019 | 3.3 |
| 1088 | 5.2 |
| 1143 | 16.7 |
| 1162 | 5.9 |
| 1208 | 3.5 |
| 1219 | 15.6 |
| 1255 | 21.3 |
| 1277 | 14.5 |
| 1292 | 8.6 |
| 1330 | 27.3 |
| 1355 | 36.1 |
| 1376 | 12.6 |
| 1386 | 3.2 |
| 1421 | 9.5 |
| 1453 | 22.5 |
| 1507 | 60.9 |
| 1561 | 100.0 |
| 1574 | 15.7 |
| 1612 | 9.8 |
| 1622 | 58.2 |
| 2242 | 29.5 |
| 2258 | 2.3 |
| 2934 | 4.6 |
| 2949 | 18.4 |
| 2963 | 2.6 |
| 2976 | 6.6 |
| 3108 | 2.9 |
| 3122 | 10.9 |
| 3146 | 5.1 |

1507, 3122, 2934, 1330 and 1255 cm$^{-1}$ are characteristic peaks for Form 2 monohydrate.

Variations, modifications, and other implementations of what is described herein will occur to those skilled in the art without departing from the spirit and the essential characteristics of the present teachings. Accordingly, the scope of the present teachings is to be defined not by the preceding illustrative description but instead by the following claims, and all changes that come within the meaning and range of equivalency of the claims are intended to be embraced therein.

Each of the printed publications, including but not limited to patents, patent applications, books, technical papers, trade publications and journal articles described or referenced in this specification are herein incorporated by reference in their entirety and for all purposes.

I claim:

1. A crystalline form of (1R,3R)-3-(cyanomethyl)-3-(4-(6-(1-methyl-1H-pyrazol-4-yl)pyrazolo[1,5-a]pyrazin-4-yl)-1H-pyrazol-1-yl)cyclobutane-1-carbonitrile, Form 1 anhydrous free base, characterized by a powder X-ray diffraction pattern comprising peaks, in terms of 2θ, at 20.6°, 22.8° and 27.0°±0.2° 2θ.

2. The crystalline form of claim 1, further characterized by a powder X-ray diffraction pattern comprising peaks, in terms of 2θ, at 18.0°, 20.6°, 22.8° and 27.0° 2θ±0.2° 2θ.

3. The crystalline form of claim 1, futher characterized by a powder X-ray diffraction pattern comprising peaks, in terms of 2θ, at 8.1°, 18.0°, 20.6°, 22.8° and 27.0° 2θ±0.2° 2θ.

4. The crystalline form of claim 1, wherein said form is non-hygroscopic.

5. The crystalline form of claim 1, wherein said form is substantially pure.

6. The crystalline form of claim 1, further characterized by a solid state $^{13}$C nuclear magnetic resonance chemical shifts selected from the group consisting of 60.2, 131.4, and 143.5 ppm±0.2 ppm.

7. The crystalline form of claim 1, further characterized by a set of Raman bands at 1246, 1498, and 2923 cm$^{-1}$±2 cm$^{-1}$.

8. The crystalline form of claim 1, further characterized by solid state $^{13}$C nuclear magnetic resonance chemical shifts of 60.2 and 131.4 ppm±0.2 ppm.

9. The crystalline form of claim 1, further characterized by a Raman band at 1498 cm$^{-1}$±2 cm$^{-1}$.

10. The crystalline form of claim 1, further characterized by a set of Raman band at 1498 cm$^{-1}$±2 cm$^{-1}$ and solid state $^{13}$C nuclear magnetic resonance chemical shifts selected from the group consisting of 60.2 and 131.4 ppm±0.2 ppm.

11. A crystalline form of (1R,3R)-3-(cyanomethyl)-3-(4-(6-(1-methyl-1H-pyrazol-4-yl)pyrazolo [1,5-a]pyrazin-4-yl)-1H-pyrazol-1-yl)cyclobutane-1-carbonitrile, Form 2 monohydrate, characterized by a powder X-ray diffraction pattern comprising peaks, in terms of 2θ, at 7.4°, 26.2°, and 28.5° 2θ±0.2° 2θ.

12. A topical formulation, comprising a crystalline form of (1R,3R)-3-(cyanomethyl)-3-(4-(6-(1-methyl-1 H-pyrazol-4-yl)pyrazolo[1,5-a]pyrazin-4yl)-1 H-pyrazol-1-yl)cyclobutane-1-carbonitrile, Form 1 anhydrous free base, characterized by a powder X-ray diffraction pattern comprising peaks, in terms of 2θ, at 20.6φ, 22.8°, and 27.0° 2θ±0.2° 2θ, and excipients suitable for transdermal administration.

13. A topical formulation, comprising a crystalline form of (1R,3R)-3-(cyanomethyl)-3-(4-(6-(1-methyl-H-pyrazol-4-yl)pyrazolo[1,5-a]pyrazin-4-yl)-1H-pyrazol-1-yl)cyclobutane-1-carbonitrile, Form 2 monohydrate, characterized by a powder X-ray diffraction pattern comprising peaks, in terms of 2θ, at 7.4°, 26.2°, and 28.5° 2θ±0.2° 2°, and excipients suitable for transdermal administration.

14. The crystalline form of claim 11, further characterized by a powder X-ray diffraction pattern comprising peaks, in terms of 2θ, at 7.4°, 15.7°, 26.2°, and 28.5° 2θ±0.2° 2θ.

15. The crystalline form of claim 11, further characterized by a powder X-ray diffraction pattern comprising peaks, in terms of 2θ, at 7.4°, 10.4°, 15.7°, 26.2°, and 28.5° 2θ±0.2° 2θ.

16. The crystalline form of claim 11, further characterized by a solid state $^{13}$C nuclear magnetic resonance chemical shifts selected from the group consisting of 130.9, 120.8, 142.8, 40.0 and 61.8 ppm±0.2 ppm.

17. The topical formulation of claim 12, wherein the amount of Form 1 anhydrous free base is in a range of about 0.1% w/v to about 5% w/v.

18. The topical formulation of claim 13, wherein the amount of Form 2 monohydrate is in a range of about 0.1% w/v to about 5% w/v.

19. The topical formulation of claim 12, wherein the topical formulation is a cream, transdermal patch, ointment, ophthalmic drops, lotion or gel.

20. The topical formulation of claim 13, wherein the topical formulation is a cream, transdermal patch, ointment, ophthalmic drops, lotion or gel.

\* \* \* \* \*